(12) United States Patent
Healy

(10) Patent No.: US 7,515,950 B2
(45) Date of Patent: Apr. 7, 2009

(54) BIOMEDICAL ELECTRODES AND BIOMEDICAL ELECTRODES FOR ELECTROSTIMULATION

(76) Inventor: James W. Healy, 280 Berry La., Sandpoint, ID (US) 83864

( * ) Notice: Subject to any disclaimer, the term of this patent is extended or adjusted under 35 U.S.C. 154(b) by 339 days.

(21) Appl. No.: 11/332,767

(22) Filed: Jan. 13, 2006

(65) Prior Publication Data

US 2006/0183989 A1     Aug. 17, 2006

Related U.S. Application Data

(60) Provisional application No. 60/643,676, filed on Jan. 13, 2005.

(51) Int. Cl.
*A61B 5/04* (2006.01)
*A61N 1/04* (2006.01)

(52) U.S. Cl. .................. 600/391; 600/392; 607/152
(58) Field of Classification Search .............. 600/391, 600/392; 607/152
See application file for complete search history.

(56) References Cited

U.S. PATENT DOCUMENTS

| | | | |
|---|---|---|---|
| 3,662,757 A * | 5/1972 | Blackett | 607/152 |
| 4,934,383 A | 6/1990 | Glumac | |
| 5,038,796 A | 8/1991 | Axelgaard et al. | |
| 5,348,007 A * | 9/1994 | Hitti | 600/391 |
| 2003/0134545 A1 | 7/2003 | McAdams et al. | |

* cited by examiner

*Primary Examiner*—Lee S Cohen
(74) *Attorney, Agent, or Firm*—Renner, Otto, Boisselle & Sklar, LLP

(57) ABSTRACT

A biomedical electrode for transmitting and/or receiving electrical signals to/from a patient is disclosed. The electrode includes a metalized fabric, wherein metallization of the fabric is connected at least on a top side and a bottom side of the fabric so as to uniformly transmit or receive the electrical signals. A conductive gel adhesive in contact with the metalized fabric. The electrode can be fabricated using a continuous web process, thereby reducing the cost of manufacturing the electrode.

5 Claims, 2 Drawing Sheets

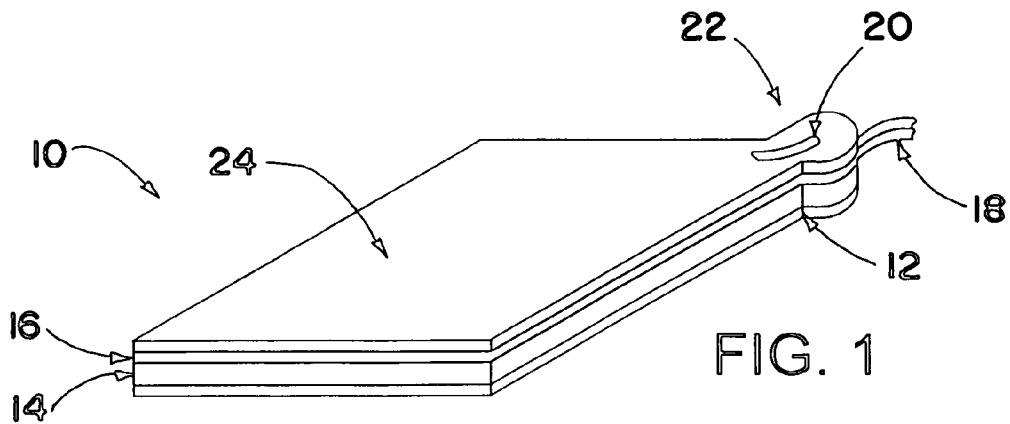
FIG. 1
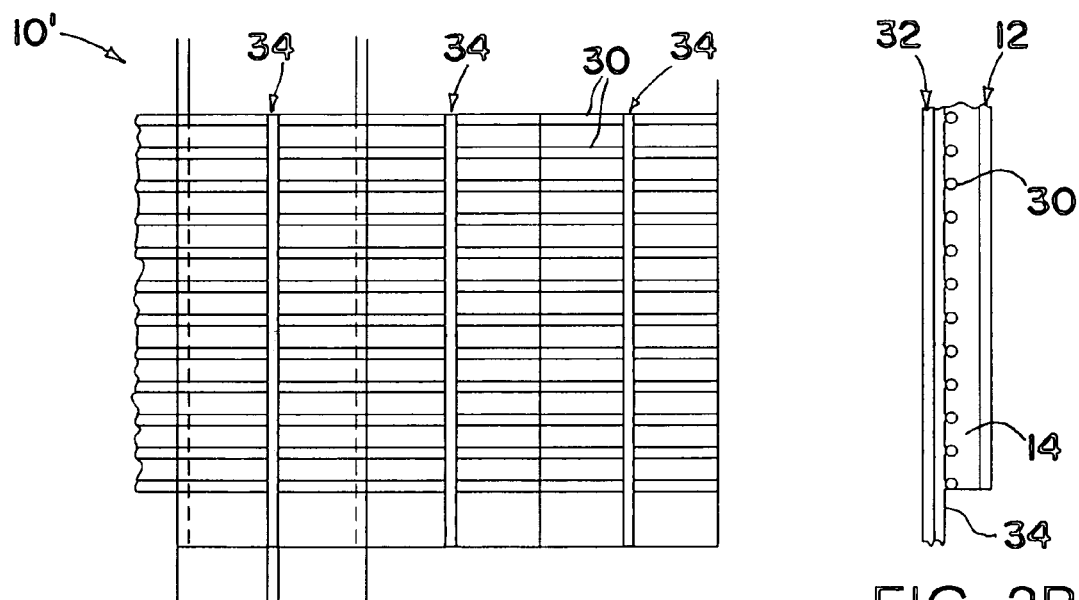
FIG. 2A
FIG. 2B
FIG. 2C
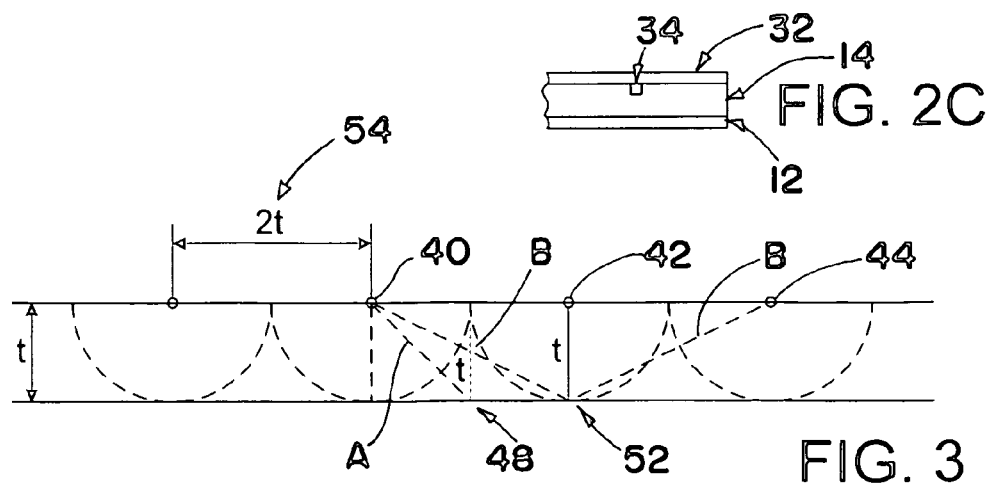
FIG. 3

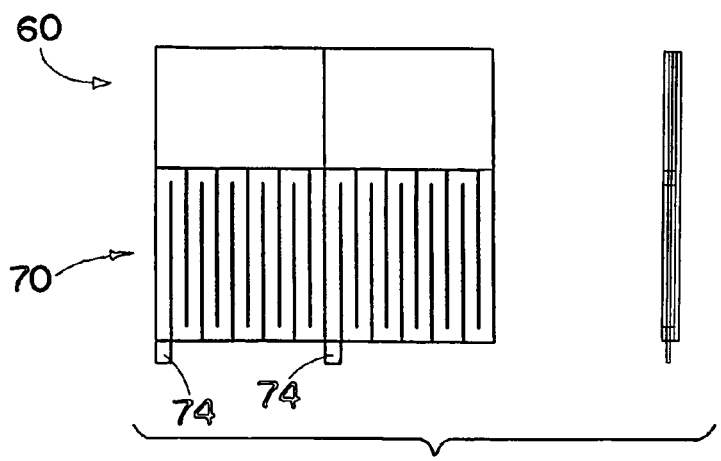
FIG. 4A
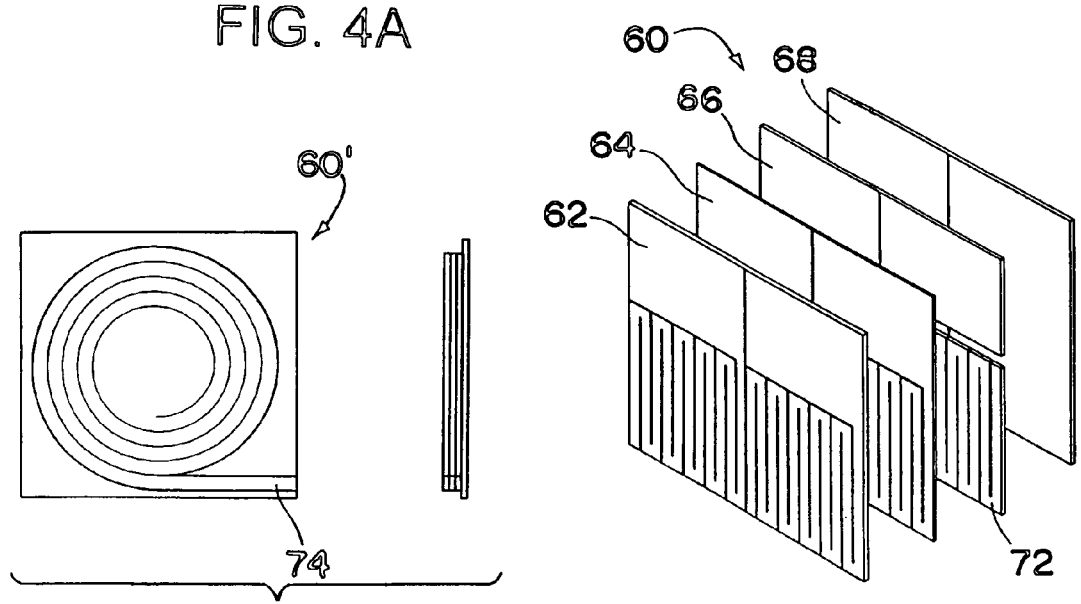
FIG. 5A
FIG. 4B
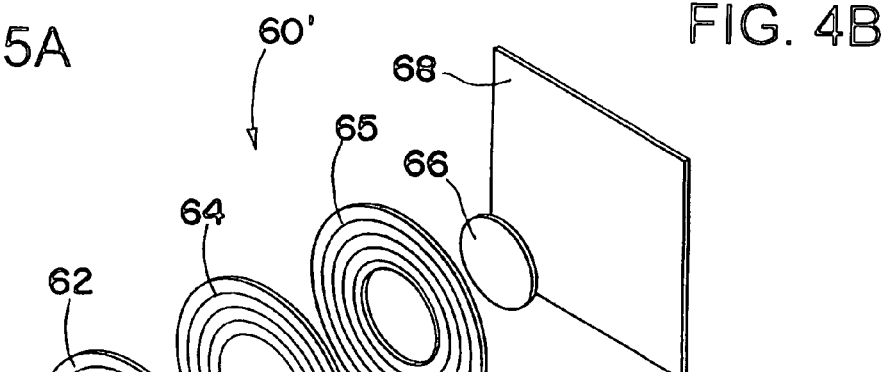
FIG. 5B

BIOMEDICAL ELECTRODES AND BIOMEDICAL ELECTRODES FOR ELECTROSTIMULATION

RELATED APPLICATION DATA

This application claims priority of U.S. Provisional Application No. 60/643,676, filed on Jan. 13, 2005, which is incorporated herein by reference in its entirety.

BACKGROUND OF THE INVENTION

There are many designs for biomedical electrodes. Typically, these electrodes include a conductive adhesive hydrogel, which is in contact with a patient's skin, a conductive material in contact with the hydrogel so as to apply a uniform voltage or current to the gel, and a wire from the conductive material to a voltage source. Additionally, the electrodes may be covered by a protective dielectric film, such as, for example, Vinyl, Polyethylene, Polystyrene and Polyester.

U.S. Patent Application Publication No. 20030134545 to McAdams teaches the use of a conductive silver ink coated on a thin substrate having a sheet resistivity of between 0.01 and 50 ohms/☐ (ohms per square). The substrate can be a polyester film or other suitable film. According to McAdams, the conductive silver coating has an irregular surface with a 4 μm peak to trough height, which could cause hot spots due to non-uniform current distribution.

U.S. Pat. No. 5,038,796 to Axelgaard discloses a conductive element that uses a weave or a knit fabric, wherein strands within the weave include stainless steel wire having a diameter of 8 microns. The wires are spaced apart from one another using a non-conducting fiber. The resulting diamond pattern of the weave provides a conductive fabric having improved stretchability and conformity around and/or between body extremities. Conductive gel fills in the interstitial space and reduces hot spots.

U.S. Pat. No. 4,934,383 to Glumac discloses a vapor deposited conductive film on polyester film. More specifically, Glumac discloses an electrode that uses a combination of a polymer film and a conductive layer to provide equalized current distribution and homogeneous impedance over the stimulating surface of the electrode. The combination of the conductive layer and polymer film can either be laminated together or vapor deposited. This enables placement of an electrical stud anywhere on the conductive layer, thereby providing for equalized current distribution.

While the above cited art presents improvements for biomedical electrodes, they each suffer from a number of technical problems. For example, the use of silver ink as disclosed in McAdams is quite inefficient. The silver flakes carried in fluid binder or ink must cause electrical tunneling in a fairly thick "0.0003" coating to be conductive. Hence, dry ink would have only a tiny fraction of the bulk conductivity of silver metal. Further, the binder and solvents in the ink can outgas and interact with the conductive gel, and the ink is quite expensive.

With respect to the technique disclosed in Axelgaard, costs can be relatively high and the resulting fabric may suffer from relatively low conductivity and uniformity. Further, production problems can arise, wherein die-cutting blades are dulled over time from cutting through the stainless steel wires. Additionally, stainless steel and other metals have a coefficient of thermal expansion of $10 \times 10^{-6}/°$ F., while plastics and polymers have expansion coefficients 2-3 times greater than metals. Due to the significantly different coefficients of thermal expansion, bowing or curling of the electrode assembly may result under some ambient thermal excursions. Also, shipping and storage may cause some delamination, resulting in potential hot spots. Embedding the fabric between two layers of gel may alleviate the problem, but will further add to the complexity of the assembly.

It is possible to use metalized films, wherein a layer of conductive material can be electrolytically deposited on a polymeric film. However, since the film (polymer) acts as a barrier, only one side is coated because there is a dielectric non-conducting film. If both sides were coated, only one side would effectively contact the gel. In any case, both the ink-coated or metalized film tends to be stiff and inflexible compared to a thin fabric.

With respect to the teachings of Glumac, a thick conductivity layer (e.g., 100-1000 Angstroms) must be deposited in order to achieve good sheet conductivity. However, these thick coatings can scratch and easily degrade, resulting in only one side being in contact with the gel.

In order to avoid hot spots (e.g., non-uniform distribution of current or voltage to the patient's skin in the area under the electrode), it is desirable to have a contacting conductive layer next to the gel that has a high conductivity. This material should be compatible with the gel, have sufficient surface area to provide good adhesive contact with the gel, be thin, flexible, stretchable, rugged and conform to body shapes, yet be easily processed, die cut and low in cost.

SUMMARY OF THE INVENTION

According to one aspect, there is provided a biomedical electrode that incorporates electrolytically plated or metalized woven ripstock, non-woven fabric, yarn and/or knitted mesh. The fabric can be thin, flexible, uniform, and highly conformable. More specifically, loosely woven or non-woven fabric can be electrolytically metalized such that it is conductive on both sides (e.g., top and bottom), and can include one or more micron thick layers of conductive metal. Further, it may be desirable to use metalized yarn in contact with the adhesive gel to provide a highly conductive means of uniformly distributing a voltage and current. The fabric can comprise a highly conductive porous material that can prevent hot spots and is superior in construction, adhesion and versatility.

These permeable and highly conductive fabrics are advantageous, for example, in that they enable superior contact with a conductive adhesive gel, and they can uniformly distribute a voltage due their higher conductivity (e.g., a resistivity>0.1 ohms/☐ for the fabric compared to 30 ohms/☐ or higher for a gel). The fabrics also are flexible and conformable, thereby enabling simplified construction and application. Further, silver coatings can be employed that are compatible with the gel and, therefore, long-term degradation of the gel/fabric interface is minimized or eliminated. The fabric can be conductive on both sides as well as through the entire fabric, allowing for good all-around conductivity and versatility in the manner in which lead wires can be connected to biomedical equipment. Additionally, the highly conductive fabric, which uniformly distributes a voltage, enables a reusable wire to be connected to each electrode (as opposed to a dedicated or permanent connection), thereby saving the time and expense associated with installation of the wires into the electrode.

According to one embodiment, there is provided a biomedical electrode for transmitting and/or receiving electrical signals to/from a patient. The electrode includes a metalized fabric, wherein metallization of the fabric is connected at least on a top side and a bottom side of the fabric so as to uniformly transmit or receive the electrical signals, and a conductive gel adhesive in contact with the metalized fabric. The electrode also can include a release liner, such as a polymer film, in contact with the conductive gel, and an adhesive dielectric fabric layer or film attached to the metalized fabric.

The metalized fabric can include at least one of metalized woven ripstock, metalized non-woven fabric, metalized knitted mesh, or metalized yarn, and can have a copper coating and a nickel over coating. Alternatively the metalized fabric can be a tin metalized fabric. Further, the metalized fabric can be a conductive porous fabric, and/or can include a silver/silver chloride (Ag/AgGI) coating having a resistivity of about 0.1 to 0.2 ohms/□.

In another embodiment, the electrode can include a tab formed on the electrode and a conductive wire lead coupled to the metalized fabric at the tab. The conductive wire can be stapled, sewn or clipped to the metalized fabric, and can be attached above or below an interface formed between the metalized fabric and the conductive gel.

In yet another embodiment, the metalized fabric of the electrode can include a metalized yarn, and adjacent threads of metalized yarn can have a spacing between about one to five times a thickness of the gel adhesive. The electrode can include a backing material in contact with the gel adhesive, and at least one conductive fabric strip can be bonded to the backing material or the gel, wherein the conductive yarn is substantially normal to the conductive fabric strip.

In another embodiment, the biomedical electrode includes a release liner, a conductive gel formed on the release liner, a conductive fabric formed on the conductive gel, and a dielectric film formed on the conductive fabric, wherein the release liner, conductive gel, conductive fabric and dielectric film are formed as a serpentine or accordion pattern. The conductive fabric can be conductive on both a top side and a bottom side of the fabric so as to uniformly transmit or receive the electrical signals, and at least one conductor can be attached to the conductive fabric. The electrode can have a spiral or round shaped.

In yet another embodiment, a method of making a biomedical electrode for transmitting and/or receiving electrical signals to/from a patient is disclosed. The method is performed using a continuous web process, including the steps of: depositing a conductive gel layer on a continuous web of release liner; placing metalized fabric layer on the layer of conductive gel; bonding a backing material to the metalized fabric layer; cutting the combined layers to form at least one electrode.

The electrode can be cut in a serpentine or accordion pattern, and the cut can be a serrated cut. Further, a dielectric coating or adhesive film can be applied on the web of material, wherein, for example, the web is dipped in the dielectric coating or the web is run through a curtain coating system.

BRIEF DESCRIPTION OF THE DRAWINGS

FIG. 1 is an isometric view of an electrode using conductive electrolytically plated fabric with a hydrogel in accordance with an embodiment of the invention.

FIG. 2A illustrates a top view of an exemplary configuration for manufacturing an electrode using conductively coated yarn, films and/or fabric in accordance with another embodiment of the invention.

FIG. 2B is a side view of the configuration of FIG. 2A.

FIG. 2C is a front view of the configuration of FIG. 2A.

FIG. 3 is a side view of conductive-coated yarn on conductive gel, wherein a current path for the conductive or metalized yarn is shown.

FIG. 4A is a front view of two electrodes side-by-side in accordance with another embodiment of the invention.

FIG. 4B is an exploded isometric view of the electrodes of FIG. 4A showing the various layers of material in the electrode.

FIGS. 5A and 5B illustrate an electrode having a die cut that forms a spiral coil for use with a round shape electrode in accordance with another embodiment of the invention.

DETAILED DESCRIPTION OF THE INVENTION

FIG. 1 illustrates an electrode 10 in accordance with an embodiment of the invention. The electrode 10 includes a first layer 12, which can be a polymer film (e.g., 5 mil PET) that operates as a release liner. The electrode 10 includes a second layer 14 in contact with the first layer 12. The second layer 14 can be a conductive gel layer, which can be purchased, for example, from Amgel Technologies, a division of Axelgaard Manufacturing, or from Procam Medical, part of Tyco International's subsidiary, Ludlow Corporation. The volume resistivity of the gel can be about 1500 ohm-cm, for example, and is available in a thickness of 35 mils.

The sheet resistivity of the gel (the second layer 14) can be determined by Equation 1, wherein W is the sheet width in centimeters, L is the sheet length in centimeters, $\rho_1$ is the volume resistivity in ohm-cm, t is the thickness in centimeters, and $\rho$ is the sheet resistivity in ohms/□.

$$\rho = \rho_1 * \frac{L}{t*W} \qquad \text{Equation 1}$$

For example, a sheet having a volume resistivity of 1500 ohm-cm, a thickness of 35 mils and a width W equal to the length L, results in a sheet resistivity of 16,873 ohms/□.

$$\frac{1500 \text{ ohm} - \text{cm}}{.035 \text{ inches} * 2.54 \text{ cm/inch}} = 16,873 \text{ ohms/□}$$

A third layer 16 of the electrode 10 is formed above the second layer 14 and comprises a metalized woven or non-woven fabric, such as ripstock or non-woven conductive material, for example. The measured sheet resistivity of various conductive metalized fabric ripstock or non-woven metalized material is about 0.1 to 0.2 ohms/□. Laird Industries sells ripstock and non-woven conductive material under the trade name Flectron. Flectron is formed from strong, flexible and conformable nylon having an overall thickness of about 0.005 inches, and is metalized with a copper coating and nickel overcoating to provide a corrosion resistant and highly conductive fabric (e.g., 0.1 ohms/□). An alternative conductive ripstock is sold by Argentum Medical, LLC under the trade name Silverlon. Alternatively, tin metalized fabric can be used as the third layer 16 in place of the above commercial offerings.

The above described conductive fabrics were developed to provide electrostatic and electromagnetic shielding for electronic components and assemblies.

Other conductive, metalized ripstock and non-woven fabric and yarns and fibers are offered by Sauquoit Industries. The metalized ripstock offered by Sauquoit Industries is metalized with a silver coating and is rugged, conformable and has a resistivity of about 0.1 ohms/□ measured on either side. Preferably, the electrode 10 utilizes a silver/silver chloride fabric ripstock as the third layer 16, although any metalized fabrics can be used. The ripstock and non-woven material is somewhat porous and provides excellent adhesion to gel or any other adhesive. Because its conductivity is more than five orders of magnitude greater than adhesive gel, the ripstock and/or non-woven fabric will distribute a current and voltage quite evenly (silver is the most conductive metal and is compatible with most gels). A conductive wire lead 18 or the like can be fastened (e.g., stapled or sewn to form a tab 20 or the like) to a corner 22 of the third layer 16 (e.g., the metalized fabric). The tab 20 can be used to pull the electrode 10 from the patient (e.g., provide a secure grasping point for removing the electrode from the patient), as shown in FIG. 1.

The ripstock and non-woven material offered by Sauquoit is quite robust, so that removal and application to a patient's skin can be accomplished using the corner wire 18 and/or tab 20. The wire 18 can be attached either below or above the gel-metalized fabric interface (e.g., above or below the interface between the second layer 14 and the third layer 16) which will reduce cost associated to standard wiring, and, as noted above, can be sewn in place, stapled or used with a conductive clip.

Because the conductive interface fabric is a polymer (nylon or polyester), thermal expansion and contraction should be the same for all components. Further, the silver/silver chloride coating in the third layer 16 according to the preferred embodiment is very conductive and thin so that the material is easily die cut without dulling knife blades. An adhesive dielectric fabric layer or film 24, such as, for example, a polyester film or other similar thin films, can be bonded to the third layer 16 or coated on the third layer 16.

Sauquolt Industries also offers a metalized yarn, which can be used to fabricate the conductive elements of the electrode in accordance with another embodiment of the invention, e.g., metalized yarn is used instead of the metalized woven fabric. The metalized yarn is offered as a metalized filament or yarn, and can be stretched 20-30% along its length. The yarn 30 will easily adhere to the conductive gel (the second layer 14) and stay in place as shown in FIG. 2A. Hence, spools of yarn may be used for a spacing width of one to five times the thickness of the gel, more preferably two to three times the thickness of the gel (i.e., the second layer 14). This is advantageous in that it will reduce material costs yet provide good conductivity. The resistivity of the yarn 30 is about twenty ohms/inch using a silver metallization.

FIGS. 2A-2C illustrate an inexpensive and preferred construction of an electrode 10' using conductive or metalized films, such as metalized yarn and metalized fabric. A coating of gel (the second layer 14) is formed on a release liner (the first layer 12), such as a woven or non-woven film (e.g., polyester). Parallel conductive coated thin film yarn 30 spaced about two times the gel thickness is formed on or placed on the gel. While a silver/silver chloride conductive yarn is a preferred material, carbon coated copper, stainless and other materials may be used. A roll of backing material 32, such as, for example, vinyl, polyethylene polystyrene or polyester, with a silver/silver chloride coated fabric strip or printed conductor 34 is bonded over the conductive coated yarn 30 and can be kiss-cut or die cut. The assembly moves from left to right while the fabric connector moves from bottom to top. The conductive fabric strip 34 can be securely bonded on the backing material 32 using, for example, pressure sensitive acrylic based adhesive or rubber based adhesive, and will make good electrical contact with the conductive yarn 30 that is normal to the fabric strip 34. Both the backing material 32 and fabric strip 34 have a large surface area so that good adhesive bonding will occur. Alternatively, the conductive fabric strip can be bonded to the gel. The electrode 10' will provide excellent stretch and conformability in all directions and a simple means of manufacturing, as it can be manufactured using a dry assembly via readily available inexpensive components. A printed silver contact may also be used in place of the fabric strip 34, but the conductive fabric strip 34 is preferable.

It is noted that the fabric assembly in accordance with the invention also can be used to fabricate EKG electrodes as shown in FIG. 1 using a roll or web construction.

FIG. 3 shows a current path for conductive or metalized yarn with 40, 42 and 44 being first, second and third yarn or wires. A first distance A is defined as the distance from conductive yarns 40 and 42 to a first point 48. A second distance B is defined as the distance from the first yarn 40 and third yarn 44 to a second point 52. The thickness of the gel is identified as t. An equapotential calculation showing the resistance distribution uniformity of parallel yarns spaced apart by two times the gel thickness can be calculated from FIG. 3 as discussed in more detail below. It is noted that the calculation is an approximation that only considers the nearest neighbor conductors.

More specifically, FIG. 3 illustrates a slice through the gel (the second layer 14) at the first and second points 48 and 52. The slice through the gel at these points can be used to determine the uniformity of the resistance, considering only nearest neighbor conductors 40 and 42 and assuming an electrode fiber space 54 is 2t, where t is the gel thickness. The first distance A or PathLength A is defined by Equation 2.

$$\text{PathLength}A = (t^2 + t^2)^{1/2} = \sqrt{2} * t \qquad \text{Equation 2}$$

The second distance B or PathLength B is defined by Equation 3.

$$\text{PathLength}B = (t^2 + (2t)^2)^{1/2} = \sqrt{5} * t \qquad \text{Equation 3}$$

Further, the resistive path for the first and second points 48 and 52 are resistances in parallel. For the first point 48, the resistance is defined by Equation 4, and for the second point 52, the resistance is defined by Equation 5.

$$\frac{1}{R_A} = \frac{1}{\sqrt{2}*t} + \frac{1}{\sqrt{2}*t} = \frac{2}{\sqrt{2}*t} = \frac{1.4}{t} \qquad \text{Equation 4}$$

$$\frac{1}{R_B} = \qquad \text{Equation 5}$$

$$\frac{1}{B} + \frac{1}{B} + \frac{1}{t} = \frac{2}{\sqrt{5}*t} + \frac{1}{\sqrt{5}*t} + \frac{1}{t} = \frac{2}{(t+\sqrt{5})} + \frac{1}{t} = \frac{1.9}{t}$$

As can be seen, the second point 52 has a slightly lower resistance path (1/1.9) than the first point 48 (1/1.4). However, they are fairly even, although it is noted again that this is a crude estimate of uniformity assuming nearest neighbor conductors.

Moving now to FIGS. 4A and 4B, there is shown an electrode 60 in accordance with another embodiment of the invention. FIG. 4A illustrates a front view of two electrodes (full size) side by side, while FIG. 4B illustrates a side perspective view of the electrodes 60 in cross section, wherein the first (dielectric layer 62), second (conductive fabric 64), third (conductive gel 66) and fourth (release line 68) layers of material within the electrode 60 can be seen. The first layer 62 may be a very thin layer of dielectric film, such as, for example, example vinyl, polyethylene, polyester, polystyrene, with adhesive on one side (e.g., pressure sensitive acrylic based adhesive or rubber based adhesive). The second layer 62 can be the conductive fabric (e.g., ripstock and/or woven and non-woven conductive materials). A rotary or other die cutter can be used to die cut a serpentine pattern 70 as shown in FIG. 4A. The die cutting may be performed so that the fabric is only partially cut (e.g., the fabric is serrated such that small pieces of the polyester or little discrete areas are not cut, leaving a weak but continuous sheet that can easily be pulled apart). A layer of dielectric coating or an adhesive film 72 can be applied on the web. This coating may be a UV "dried" dielectric or a flexible latex coating, for example. The serpentine or coil 70 may be extended, then dipped in the dielectric coating 72 or run through a curtain coating system, leaving a connector portion 74 exposed. A thick gel coating (the third layer 66) may be applied or a laminate of thick Mylar (the fourth layer 68) and conductive gel may be laminated to conductive fabric 62. After the die cutting operation, a male conductor 74 can be attached, and also may be coated. A final die cut may be made for the separation of the electrodes 60.

FIGS. 5A and 5B illustrate another embodiment of an electrode 60' in accordance with the invention. The electrode 60' uses a different die cut that provides a spiral coil for a round-shape electrode. Additional configurations may be made by varying the die cuts. The electrode 60' includes a first dielectric layer 62, a conductive fabric layer 64, a second dielectric layer 65, a conductive gel layer 66, and a release liner 68. A conductor 74 as attached to an end of the electrode 60'.

The basic concept uses in-line web production for all layers and assembly, which greatly reduces cost. The electrodes may be of any size and may be round, square or any other shape. The serpentine die cut can be of any size, such as, for example, from 1/32" to 1/2" wide. This results in a "wire" or connector of any length depending on the die cut and the size of the electrode.

In the example shown in FIG. 4A, the electrodes are approximately 1 3/8" wide by 1" long. The serpentine die cut material is 1/8" wide. This results in a "wire" or connector 1/8" wide by (11)(1.5) or 1.8"×16.5" long.

The resistance of the "wire" or serpentine die cut is the fabric resistivity, e.g., about 0.1 ohms/□. Thus, for a serpentine die cut having a length of 16.5 inches and a width of 0.125 inches, the resistance would be 13.2 ohms.

$$R = \Box \cdot L/W = 0.1 \cdot 16.5(8) = 1.65(8) = 13.2 \text{ ohms}$$

Typically the resistance of the gel skin interface is 30 ohms or higher and, thus, the resistance of the wire is a small percentage of the electrode. The advantages of this design are many. For example:

1) The fabric is highly conductive and flexible so that "unwinding" of the die cut wire can be easily accomplished without introducing kinks into the wire. Further, the unwound wire is flexible and not springy.
2) The wire is part of the electrode, which assures excellent, reliable and rugged electrical contact.
3) The voltage applied to the patient or the signal picked up from the patient is uniformly applied or received from the skin even though the electrical contact is in a corner of the electrode. This advantage is due in part to high conductivity of the fabric and the lower conductivity of the gel.
4) Roll to roll production reduces cost and facilitates high production with very little labor cost.
5) The cost of attaching a wire and the wire costs (which are large) associated with conventional electrodes are reduced or eliminated.
6) The cost of the fabric is about $0.004 or 0.4 cents per inch$^2$. Hence, for the example in FIG. 1 the material cost would be 1.5×1 3/8×0.4=0.825 cents≈1 cent.
7) A flat electrode and wire enable simple assembly that is easy to package and much more user-friendly, e.g., the user doesn't have to handle or unwind wires.
8) The "wire" can have a dielectric coating on all sides, and if the flexible latex dielectric coating is applied after the die cutting, it will tend to conform and seal edges that have been die cut.

It should be noted that while an example of a fabricated electrode is shown, many other configurations may be used. Further, in the example given, the steps may be altered and the first layer 62 may be a heavy dielectric coating.

Although the invention has been shown and described with respect to a certain preferred embodiment or embodiments, it is obvious that equivalent alterations and modifications will occur to others skilled in the art upon the reading and understanding of this specification and the annexed drawings. In particular regard to the various functions performed by the above described elements (components, assemblies, devices, compositions, etc.), the terms (including a reference to a "means") used to describe such elements are intended to correspond, unless otherwise indicated, to any element which performs the specified function of the described element (i.e., that is functionally equivalent), even though not structurally equivalent to the disclosed structure which performs the function in the herein illustrated exemplary embodiment or embodiments of the invention. In addition, while a particular feature of the invention may have been described above with respect to only one or more of several illustrated embodiments, such feature may be combined with one or more other features of the other embodiments, as may be desired and advantageous for any given or particular application.

What is claimed is:

1. A biomedical electrode for transmitting and/or receiving electrical signals to/from a patient, comprising:
    a release liner;
    a conductive gel formed on the release liner;
    a conductive layer formed on the conductive gel; and
    a dielectric film formed on the conductive layer, wherein the release liner conductive gel, conductive layer and dielectric film are formed as a serpentine pattern.

2. The electrode of claim 1, further comprising at least one conductor attached to the conductive layer.

3. The electrode of claim 1, wherein the conductive layer is conductive on both a top side and a bottom side of the layer so as to uniformly transmit or receive the electrical signals.

4. The electrode of claim 1, wherein the electrode is formed as a spiral or round shape.

5. A biomedical electrode for transmitting and/or receiving electrical signals to/from a patient, comprising:
    a release liner;
    a conductive gel formed on the release liner;
    a conductive layer formed on the conductive gel; and
    a dielectric film formed on the conductive layer, wherein the release liner, conductive gel, conductive layer and dielectric film are formed as an accordion pattern.

* * * * *